US011330984B2

(12) United States Patent
Le et al.

(10) Patent No.: US 11,330,984 B2
(45) Date of Patent: May 17, 2022

(54) WEARABLE GRAPHENE SENSORS

(71) Applicants: THE TRUSTEES OF THE STEVENS INSTITUTE OF TECHNOLOGY, Hoboken, NJ (US); FLEXTRAPOWER, INC., Long Island City, NY (US)

(72) Inventors: Linh Tung Le, New York, NY (US); Trung Thanh Dinh-Trong, Bedminster, NJ (US); Woo Young Lee, Lyndhurst, NJ (US); Eric Peter Boon, Jersey City, NJ (US); Nguyen An Nguyen, New York, NY (US)

(73) Assignees: THE TRUSTEES OF THE STEVENS INSTITUTE OF TECHNOLOGY, Hoboken, NJ (US); FLEXTRAPOWER, INC., Long Island City, NY (US)

( * ) Notice: Subject to any disclaimer, the term of this patent is extended or adjusted under 35 U.S.C. 154(b) by 654 days.

(21) Appl. No.: 15/185,411

(22) Filed: Jun. 17, 2016

(65) Prior Publication Data
US 2016/0367151 A1 Dec. 22, 2016

Related U.S. Application Data

(60) Provisional application No. 62/182,097, filed on Jun. 19, 2015.

(51) Int. Cl.
*A61N 1/04* (2006.01)
*A61B 5/05* (2021.01)
(Continued)

(52) U.S. Cl.
CPC .................. *A61B 5/01* (2013.01); *G01K 7/16* (2013.01); *G01L 1/20* (2013.01); *A61B 5/0008* (2013.01);
(Continued)

(58) Field of Classification Search
CPC ...... A61N 1/04; A61N 1/0436; A61N 1/0492; A61B 2562/0285; A61B 2562/164;
(Continued)

(56) References Cited

U.S. PATENT DOCUMENTS 4,772,924 A 9/1988 Bean et al.
4,903,101 A 2/1990 Maserjian
(Continued)

FOREIGN PATENT DOCUMENTS

WO 2012073998 6/2013
WO 2013119295 8/2013

OTHER PUBLICATIONS

Lam et al."MWCNT/Cotton-Based Flexible Electrode for Electrocardiography" IEEE. 2013 (Year: 2013).*
(Continued)

*Primary Examiner* — Joseph A Stoklosa
*Assistant Examiner* — Brian M Antiskay
(74) *Attorney, Agent, or Firm* — Lewis Roca Rothgerber Christie LLP

(57) ABSTRACT

A sensing system includes a sensor including a flexible substrate and a graphene oxide sensing element deposited on the flexible substrate. The graphene oxide sensing element has first and second sides. First and second electrical connectors coupled to the first and second sides of the graphene oxide sensing element, respectively. A power source is coupled to the first and second electrical connectors of the sensor and is adapted to apply a constant voltage to the sensor. The sensing system also includes a measurement element measuring a current in the graphene oxide sensing element due to the constant voltage and a calculation element calculating an electrical resistance of the graphene oxide sensing element based on the electrical current and the constant voltage and calculating a condition at a location of
(Continued)

the sensor based on a relationship between the electrical resistance and the condition for the graphene oxide sensing element.

16 Claims, 12 Drawing Sheets

(51) Int. Cl.
| | | |
|---|---|---|
| *A61B 5/01* | (2006.01) | |
| *G01K 7/16* | (2006.01) | |
| *G01L 1/20* | (2006.01) | |
| *A61B 5/024* | (2006.01) | |
| *A61B 5/00* | (2006.01) | |
| *A61B 5/25* | (2021.01) | |

(52) U.S. Cl.
CPC ............ *A61B 5/02444* (2013.01); *A61B 5/25* (2021.01); *A61B 5/6843* (2013.01); *A61B 2562/164* (2013.01)

(58) Field of Classification Search
CPC ....... A61B 5/01; A61B 5/6833; A61B 5/0028; A61B 5/04; A61B 5/0402; A61B 5/0476; A61B 2018/00452; A61B 2018/1465; A61B 2090/065; A61B 2562/227; A61B 5/0004; A61B 5/0245; A61B 5/11
USPC ................ 600/372, 382–384, 386–393, 395, 600/508–509, 527, 529, 547; 607/6, 8, 607/115, 119
See application file for complete search history.

(56) References Cited

U.S. PATENT DOCUMENTS

| | | | |
|---|---|---|---|
| 5,238,868 A | 8/1993 | Elman et al. | |
| 6,813,064 B2 | 11/2004 | John et al. | |
| 7,167,355 B2 | 1/2007 | Chen | |
| 7,217,951 B2 | 5/2007 | Krishna et al. | |
| 7,387,253 B1 | 6/2008 | Parker et al. | |
| 7,550,755 B2 | 6/2009 | Balkenende et al. | |
| 7,628,928 B2 | 12/2009 | Guerra | |
| 7,830,926 B1 | 11/2010 | Kim | |
| 7,852,613 B2 | 12/2010 | Ma et al. | |
| 8,098,482 B2 | 1/2012 | Clelland et al. | |
| 8,206,469 B2 | 6/2012 | Chiang et al. | |
| 8,278,757 B2 | 10/2012 | Crain | |
| 8,455,842 B2 | 6/2013 | Zhang | |
| 8,697,485 B2 | 4/2014 | Crain | |
| 8,810,996 B2 | 8/2014 | Lee et al. | |
| 8,878,120 B2 | 11/2014 | Patil et al. | |
| 9,025,316 B2 | 5/2015 | Lee et al. | |
| 9,165,721 B2 | 10/2015 | Lee et al. | |
| 9,178,129 B2 | 11/2015 | Lee et al. | |
| 10,001,614 B2* | 6/2018 | Gao | ............... H01B 7/046 |
| 2003/0012249 A1 | 1/2003 | Eisenbeiser | |
| 2007/0215855 A1 | 9/2007 | Kang | |
| 2008/0021339 A1* | 1/2008 | Gabriel | ............... A61B 5/0833 |
| | | | 600/532 |
| 2010/0207254 A1 | 8/2010 | Jain et al. | |
| 2011/0042813 A1 | 2/2011 | Crain | |
| 2011/0052813 A1 | 3/2011 | Ho | |
| 2011/0101309 A1 | 5/2011 | Lin et al. | |
| 2012/0007913 A1 | 1/2012 | Jang | |
| 2012/0121891 A1 | 5/2012 | Kim | |
| 2012/0128983 A1 | 5/2012 | Yoon | |
| 2012/0170171 A1* | 7/2012 | Lee | ............... H01G 11/36 |
| | | | 361/502 |
| 2012/0235119 A1 | 9/2012 | Babich et al. | |
| 2012/0244358 A1 | 9/2012 | Lock | |
| 2012/0255860 A1 | 10/2012 | Briman et al. | |
| 2012/0270205 A1 | 10/2012 | Patel | |
| 2013/0264011 A1 | 10/2013 | Lin | |
| 2013/0264192 A1 | 10/2013 | Lin | |
| 2013/0264193 A1 | 10/2013 | Lin | |
| 2013/0264307 A1 | 10/2013 | Lin | |
| 2013/0266729 A1 | 10/2013 | Lin | |
| 2013/0295374 A1* | 11/2013 | Tang | ............... B82B 1/002 |
| | | | 428/323 |
| 2013/0345539 A1* | 12/2013 | Quintanar | ............ A61B 5/6822 |
| | | | 600/385 |
| 2014/0103298 A1* | 4/2014 | Lee | ............... G01K 7/22 |
| | | | 257/29 |
| 2014/0127584 A1 | 5/2014 | Kim et al. | |
| 2014/0205841 A1 | 7/2014 | Qiu et al. | |
| 2014/0231002 A1 | 8/2014 | Patil et al. | |
| 2014/0303470 A1* | 10/2014 | Tsukada | ............... D06P 1/38 |
| | | | 600/377 |
| 2014/0321028 A1 | 10/2014 | Lee et al. | |
| 2014/0364712 A1* | 12/2014 | Lam | ............... C01B 32/184 |
| | | | 600/369 |
| 2015/0250420 A1* | 9/2015 | Longinotti-Buitoni | ............... |
| | | | A61B 5/6804 |
| | | | 600/301 |
| 2016/0198996 A1* | 7/2016 | Dullen | ............... A61B 5/0024 |
| | | | 600/301 |
| 2016/0287175 A1* | 10/2016 | Coleman | ............... C08K 3/01 |
| 2017/0350882 A1* | 12/2017 | Lin | ............... A61B 5/6821 |

OTHER PUBLICATIONS

Li et al. "From cotton to wearable pressure sensor". Journal of Materials Chemistry A. Nov. 2014. (Year: 2014).*
Park et al. "Highly Stretchable and Wearable Graphene Strain Sensors with Controllable Sensitivity for Human Motion Monitoring". ACS Appl. Mater. Interfaces 2015, 7, 6317-6324. Mar. 2015. (Year: 2015).*
Zhou, M. et al., Controlled Synthesis of Large-Area and Patterned Electrochemically Reduced Graphene Oxide Films, Chem. Eur. J., 2009, 15, pp. 6116-6120.
Zhu, Y. et al., Carbon-Based Supercapacitors Produced by Activation of Graphene; Science, 332 (2011) 1537-1541.
Akhavan, O. et al., Toxicity of graphene and graphene oxide nanowalls against bacteria, ACS Nano, 4 (2010) 5731-5736.
An et al., Optical and Sensing Properties of 1-Pyrenecarboxylic Acid-Functionalized Graphene Films laminated on Polydimethylsiloxane Membrane, American Chemical Society, vol. 5, No. 2, (2011), pp. 1003-1011.
Bolotin, K. et al., Ultrahigh electron mobility in suspended graphene; Solid State Communications, 146 (2008) 351-355.
Bourlinos, A. et al., Graphite oxide: Chemical reduction to graphite and surface modification with primary aliphatic amines and amino acids, Langmuir, 19 (2003) 6050-6055.
Chen, Z. et al., Three-dimensional flexible and conductive interconnected graphene networks grown by chemical vapour deposition, Nature Materials, 10 (2011) 424-428.
Cho, S. et al., Enhanced efficiency of organic light emitting devices (OLEDs) by control of laser imaging condition; Organic Electronics 13 (2012) 833-839.
Coleman, J.N., Liquid-Phase Exfoliation of Nanotubes and Graphene, Advanced Functional Materials, 19 (2009) 3680-3695.
Cote, L. et al., Flash Reduction and Patterning of Graphite Oxide and Its Polymer Composite, Journal of the American Chemical Society, 131(2009)11027-11032.
Dikin, D. et al., Preparation and characterization of graphene oxide paper, Nature, 448 (2007) 457-460.
Dreyer, D. et al., From Conception to Realization: An Historical Account of Graphene and Some Perspectives for Its Future, Angewandte Chemie International Edition, 49 (2010) 9336-9344.
Dreyer, D. et al., The chemistry of graphene oxide, Chemical Society reviews, 39 (2010) 228-240.
El-Kady, M. et al., "Laser Scribing of High-Performance and Flexible Graphene-Based Electrochemical Capacitors," Science, vol. 335, No. 6074, pp. 1326-1330, Mar. 2012.
Gao, X. et al., Hydrazine and thermal reduction of graphene oxide: Reaction mechanisms, product structures, and reaction design, Journal of Physical Chemistry C, 114 (2010) 832-842.

(56) References Cited

OTHER PUBLICATIONS

Havener, R. et al., Hyperspectral Imaging of Structure and composition in Atomically Thin Heterostructures; ACS Nano, 13 (2013) 3942-3946.
Hong, A. et al., "Graphene Flash Memory," ACS Nano 5 (10), 7812-7817 (2011).
Huang et al., Graphene-Based Conducting Inks for Direct Inkjet Printing of Flexible Conductive Patterns and Their Applications in Electric Circuits and Chemical Sensors, Nano Res, (2011), 10 pages.
Jacoby, Graphene Moves Toward Applciations, www.cen-online.org, Nov. 21, 2011, pp. 10-15.
Jang, B.Z. et al., Processing of nanographene platelets (NGPs) and NGP nanocomposites: a review; Journal of Materials Science 43, 5092-5101, (2008).
Kim, F. et al., Graphene oxide: Surface activity and two-dimensional assembly, Advanced Materials, 22 (2010) 1954-1958.
Kim, J. et al., Graphene oxide sheets at interfaces, Journal of the American Chemical Society, 132 (2010) 8180-8186.
Ko, S. et al., Unconventional, Laser Based OLEO Material Direct Patterning and Transfer Method; Organic Light Emitting Diode—Material, Process and Devices; Intech, ISBN: 978-953-307-273-9.
Kong, D. et al., Temperature-Dependent Electrical Properties of Graphene Inkjet-Printed on Flexible Materials, Langmuir, ACS Publications, American Chemical Society, 28, (2012) pp. 13467-13472.
Le et al., Graphene supercapacitor electrodes fabricated by inkjet printing and thermal reduction of graphene oxide, Electrochemistry Communications, vol. 13, (2011), pp. 355-358.
Le et al., Inkjet-Printed Graphene for Flexible Micro-Supercapacitors, IEEE International Conference on Nanotechnology, Aug. 15-18, 2011, Portland, Oregon, USA, pp. 67-71.
Lee, K. et al., Effect of Laser Beam Trajectory on Donor Plate in Laser Induced Thermal Printing Process; Journal of the Optical Society of Korea, vol. 15, No. 4, Dec. 2011, pp. 362-367.
Lee, Y. et al., "Wafer-Scale Synthesis and Transfer of Graphene Films," Nano Letters 10 (2), 490-493 (2010).
Li, D. et al., Processable aqueous dispersions of graphene nanosheets, Nat Nano, 3 (2008) 101-105.
Li, X. et al., Large-Area Synthesis of High-Quality and Uniform Graphene Films on Copper Foils, Science, 324 (2009) 1312-1314.
Lin, Y. et al., "100-GHz Transistors from Wafer-Scale Epitaxial Graphene," Science, 327 (2010) p. 662.
Lin, Y. et al., "Wafer-Scale Graphene Integrated Circuit," Science 332 (6035), 1294-1297 (2011).

Liu, C. et al., Graphene-Based Supercapacitor with an Ultrahigh Energy Density; NanoLetters, 10, 4863-4868, (2010).
Luo, J. et al., Compression and Aggregation-Resistant Particles of Crumpled Soft Sheets, ACS Nano, 5 (2011) 8943-8949.
Luo, J. et al., Graphene oxide nanocolloids, Journal of the American Chemical Society, 132 (2010) pp. 17667-17669.
Novoselov, K. et al., Electric Field Effect in Atomically Thin Carbon Films, Science, 306 (2004) pp. 666-669.
Olivares-Marin, M. et al., Cherry stones as precursor of activated carbons for supercapacitors; Materials Chemistry and Physics 114, 1, (2009) 223-227.
Park, J. et al., Multi-scale graphene patterns on arbitrary substrates via laser-assisted transfer-printing process, Applied Physics Letters, vol. 101, No. 4, (2012) p. 043110-043110-4.
Park, S. et al., Chemical methods for the production of graphenes, Nat Nano, 4 (2009) 217-224.
Product literature for Arduino Micro by Arduino LLC, <https://www.arduino.cc/en/Main/ArduinoBoardMicro>, retrieved Aug. 4, 2016.
Product literature for Arduino Uno by Arduino LLC, <https://www.arduino.cc/en/Main/ArduinoBoardUno>, retrieved Aug. 4, 2016.
Product literature dated Mar. 2012 for Kapton material by DuPont.
Product literature dated 2014 for Parylene-D material by Specialty Coating Systems.
Product literature for Pulse Sensor Amped by Adafruit Industries <https://pulse-sensor.googlecode.com/files/PulseSensorAmpedGettingStartedGuide.pdf>.
Shao, G. et al., Graphene oxide: The mechanisms of oxidation and exfoliation, Journal of Materials Science, 47 (2012) 4400-4409.
Stankovich, S. et al., Synthesis of graphene-based nanosheets via chemical reduction of exfoliated graphite oxide, Carbon, 45 (2007) 1558-1565.
Stoller, M. et al., Graphene-Based ultracapacitors; Nano Letters, 8 (2008) 3498-3502.
Torrisi, F. et al., Inkjet-Printed Graphene Electronics, ACS NANO, vol. 6, No. 4, (2012) 2992-3006.
Wu, Z.S. et al., Graphene/metal oxide composite electrode materials for energy storage, Nano Energy, 1 (2012) 107-131.
Zangmeister, C.D., Preparation and evaluation of graphite oxide reduced at 220 c, Chemistry of Materials, 22 (2010) 5625-5629.
Zhang, Y. et al., "Direct imprinting of microcircuits on graphene oxides film by femtosecond laser reduction," Nano Today, vol. 5, (2010) pp. 15-20.
Zhang, Y. et al., Cytotoxicity effects of graphene and single-wall carbon nanotubes in neural phaeochromocytoma-derived pc12 cells, ACS Nano, 4 (2010) 3181-3186.

\* cited by examiner

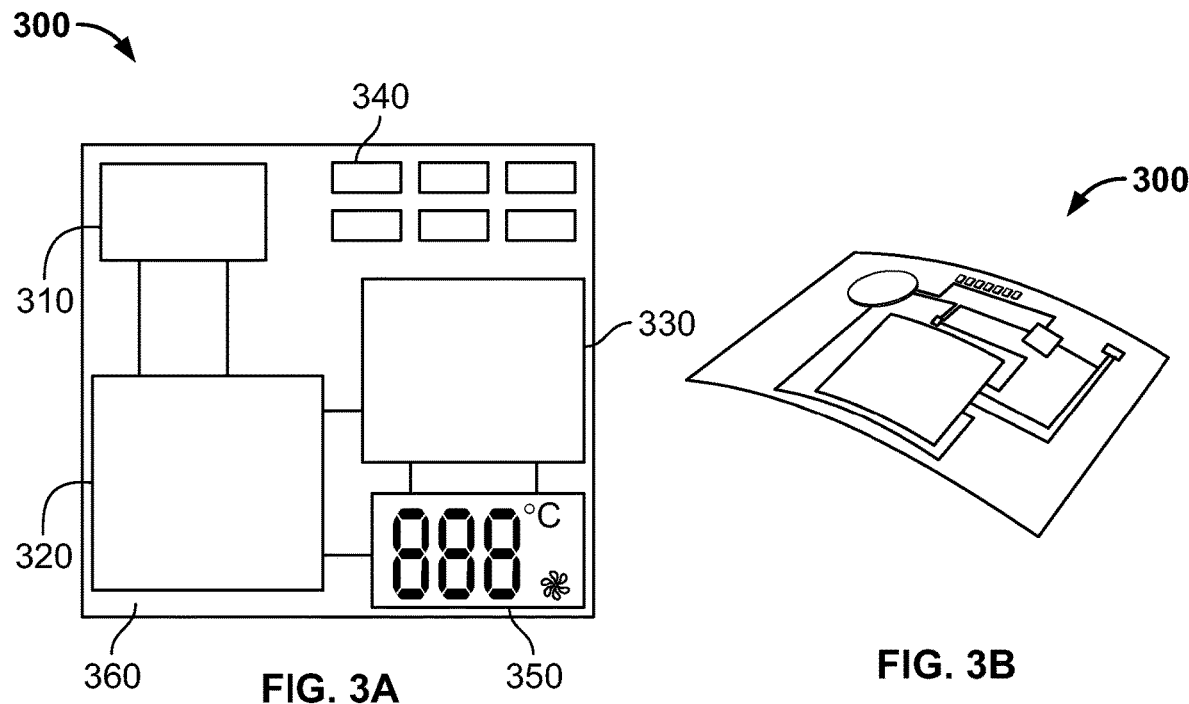
FIG. 3A
FIG. 3B
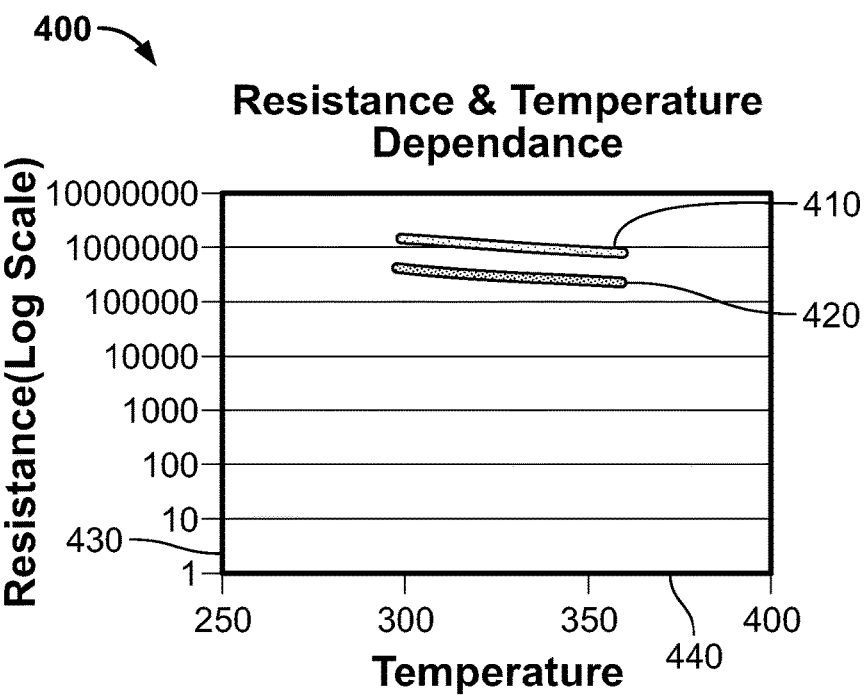
FIG. 4

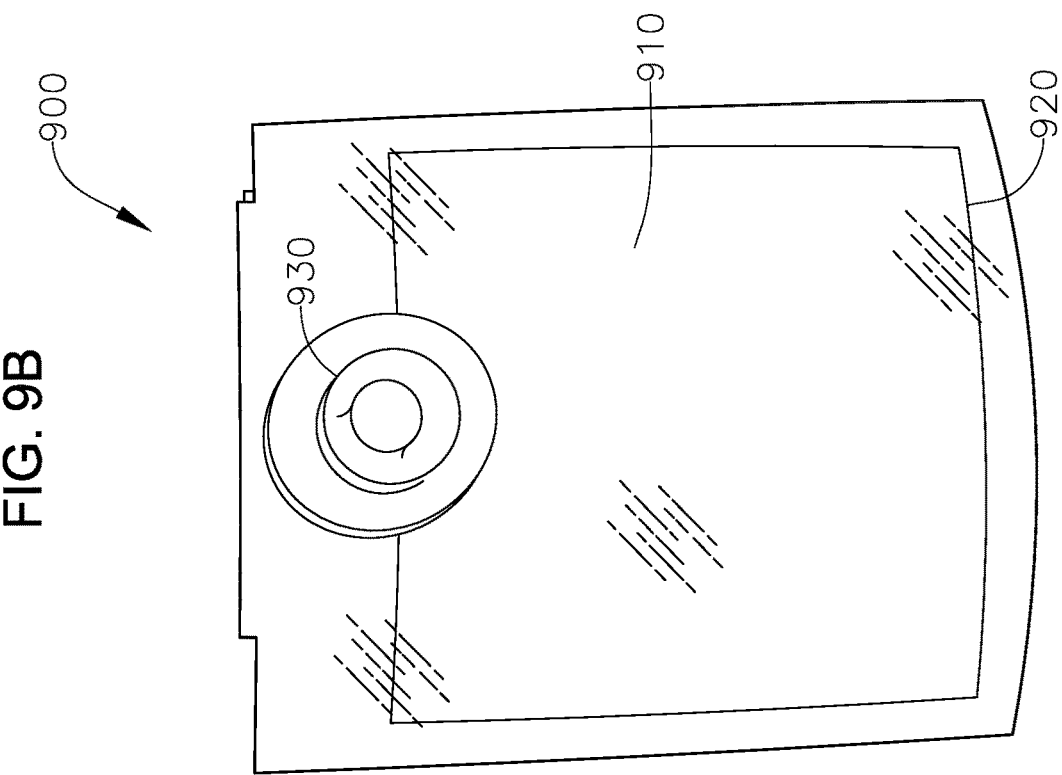
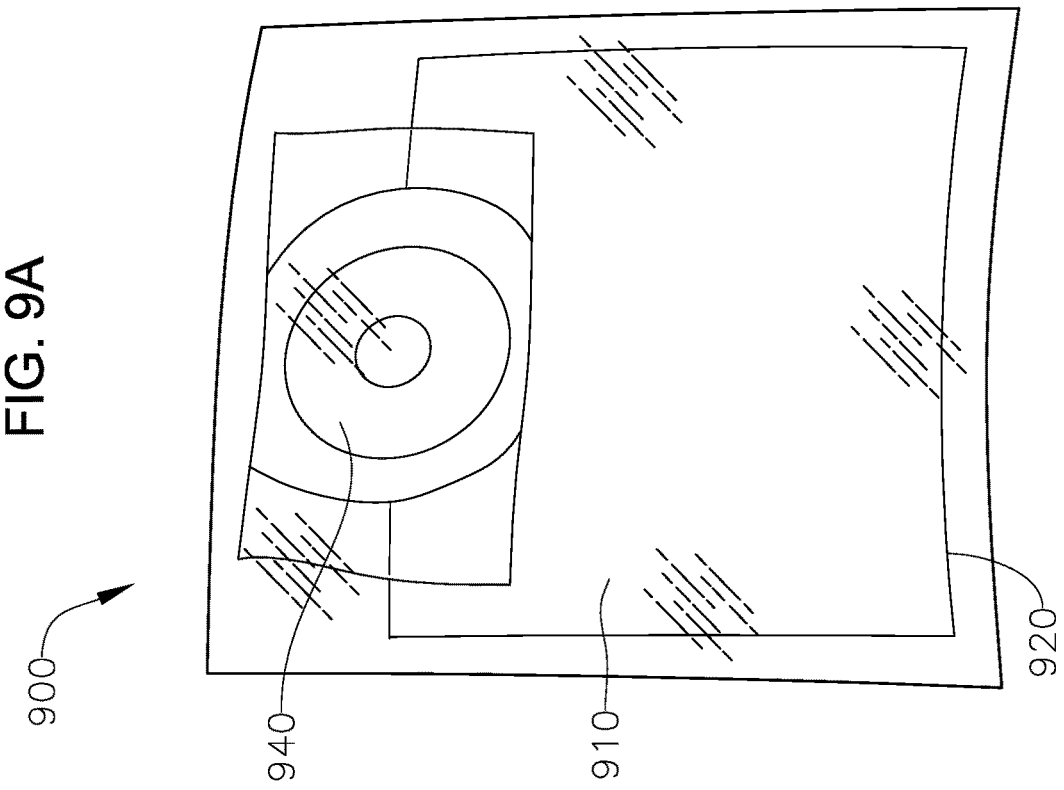

WEARABLE GRAPHENE SENSORS

CROSS-REFERENCE TO RELATED APPLICATION

This application is a Section 111(a) application relating to and claiming the benefit of commonly owned, U.S. Provisional Patent Application No. 62/182,097, titled "WEARABLE GRAPHENE SENSORS FOR PHYSIOLOGICAL MONITORING," having a filing date of Jun. 19, 2015, which is incorporated by reference herein in its entirety.

FIELD OF THE INVENTION

The exemplary embodiments relate generally to graphene oxide sensors and, more specifically, to graphene oxide sensors monitoring a condition at a location of the sensors based on electrical resistance of the sensors at the time of sensing.

BACKGROUND OF THE INVENTION

Graphene oxide can be used to fabricate highly flexible electrically conductive films, which may be useful in various applications ranging from optoelectronics to energy storage to biomedical devices. Techniques for inkjet printing of a dispersed graphene oxide sheet and for subsequent reduction thereof to graphene for use as supercapacitor electrodes are described in co-owned U.S. Pat. No. 8,810,996, the entirety of which is incorporated herein by reference.

SUMMARY OF THE INVENTION

In an embodiment, a sensing system includes a sensor including a flexible substrate and a graphene oxide sensing element deposited on the flexible substrate. The graphene oxide sensing element has a first side and a second side opposite the first side. The sensor also includes a first electrical connector coupled to the first side of the graphene oxide sensing element and a second electrical connector coupled to the second side of the graphene oxide sensing element. The sensing system also includes a power source coupled to the first and second electrical connectors of the sensor. The power source is adapted to apply a constant voltage to the sensor. The sensing system also includes a measurement element measuring an electrical current in the graphene oxide sensing element due to the constant voltage and a calculation element including a non-transitory computer-readable storage medium storing a set of instructions and a processor operative to execute said set of instructions. The set of instructions, when executed by the processor, causes the processor to calculate an electrical resistance of the graphene oxide sensing element based on the electrical current and the constant voltage and to calculate a condition at a location of the sensor based on a relationship between the electrical resistance and the condition for the graphene oxide sensing element.

In an embodiment, the condition is a temperature. In an embodiment, the processor determines the temperature based on a linear relationship between a natural logarithm of the electrical resistance of the sensing element and an inverse of the temperature. In an embodiment, the flexible substrate is adapted to be affixed to a person's skin. In an embodiment, the processor calculates a plurality of temperatures. Each of the temperatures is calculated at a corresponding one of a plurality of times. In an embodiment, the processor determines a pulse rate for the person based on the plurality of temperatures. In an embodiment, the processor generates an electrocardiogram signal for the person based on at least the temperature.

In an embodiment, the condition is a pressure. In an embodiment, the graphene oxide sensing element includes a first graphene oxide element and a second graphene oxide sensing element overlaying the first graphene oxide sensing element.

In an embodiment, a method of determining a condition at a location includes the steps of providing, at a target location, a sensing element including a graphene oxide sensing element deposited on a substrate; determining at least one resistance of the sensing element; and determining a value of the condition at the target location based on each of the at least one resistance of the sensing element.

In an embodiment, the condition is a temperature. In an embodiment, the step of determining at least one resistance of the sensing element comprises measuring a plurality of resistances of the sensing element. Each of the plurality of resistances is measured at a corresponding one of a plurality of times. The step of determining a condition at the target location based on each of the at least one resistance of the sensing element comprises determining a plurality of temperatures at the target location. Each of the plurality of temperatures is determined based on a corresponding one of the plurality of resistances of the sensing element. In an embodiment, the method also includes the step of generating a time series based on the plurality of temperatures and the plurality of times. In an embodiment, the target location is a portion of a person's skin and the method also includes the step of determining a pulse rate of the subject based on the time series. In an embodiment, the target location is an electrocardiogram electrode attachment location on a person's skin, and the method also includes the step of generating an electrocardiogram signal based on at least the time series.

In an embodiment, the condition is a pressure.

In an embodiment, a sensor includes a flexible substrate and a graphene oxide sensing element deposited on the flexible substrate. The graphene oxide sensing element has a first side and a second side opposite the first side. The sensor also includes a first electrical connector coupled to the first side of the graphene oxide sensing element and a second electrical connector coupled to the second side of the graphene oxide sensing element.

In an embodiment, the flexible substrate is made from one of a polyester and a polyimide. In an embodiment, the flexible substrate is a fiber. In an embodiment, the graphene oxide sensing element is deposited on the flexible substrate by inkjet printing a graphene oxide solution on the flexible substrate.

BRIEF DESCRIPTION OF FIGURES

FIG. 3A is a schematic illustration of a third exemplary sensing system including a third exemplary graphene oxide sensing element;

FIG. 3B is a perspective view of the exemplary sensing system of FIG. 3A;

FIG. 4 is a graph showing the correlation between resistance and temperature for an exemplary sensing element including a graphene oxide thin film exhibiting negative temperature coefficient ("NTC") behavior;

FIG. 9A is a photograph of a fourth exemplary graphene oxide sensing element, shown from a side that is adapted to contact a person's skin;

FIG. 9B is a photograph of the sensing element of FIG. 9A, shown from an opposite side;

DETAILED DESCRIPTION OF THE INVENTION

Figure 1:
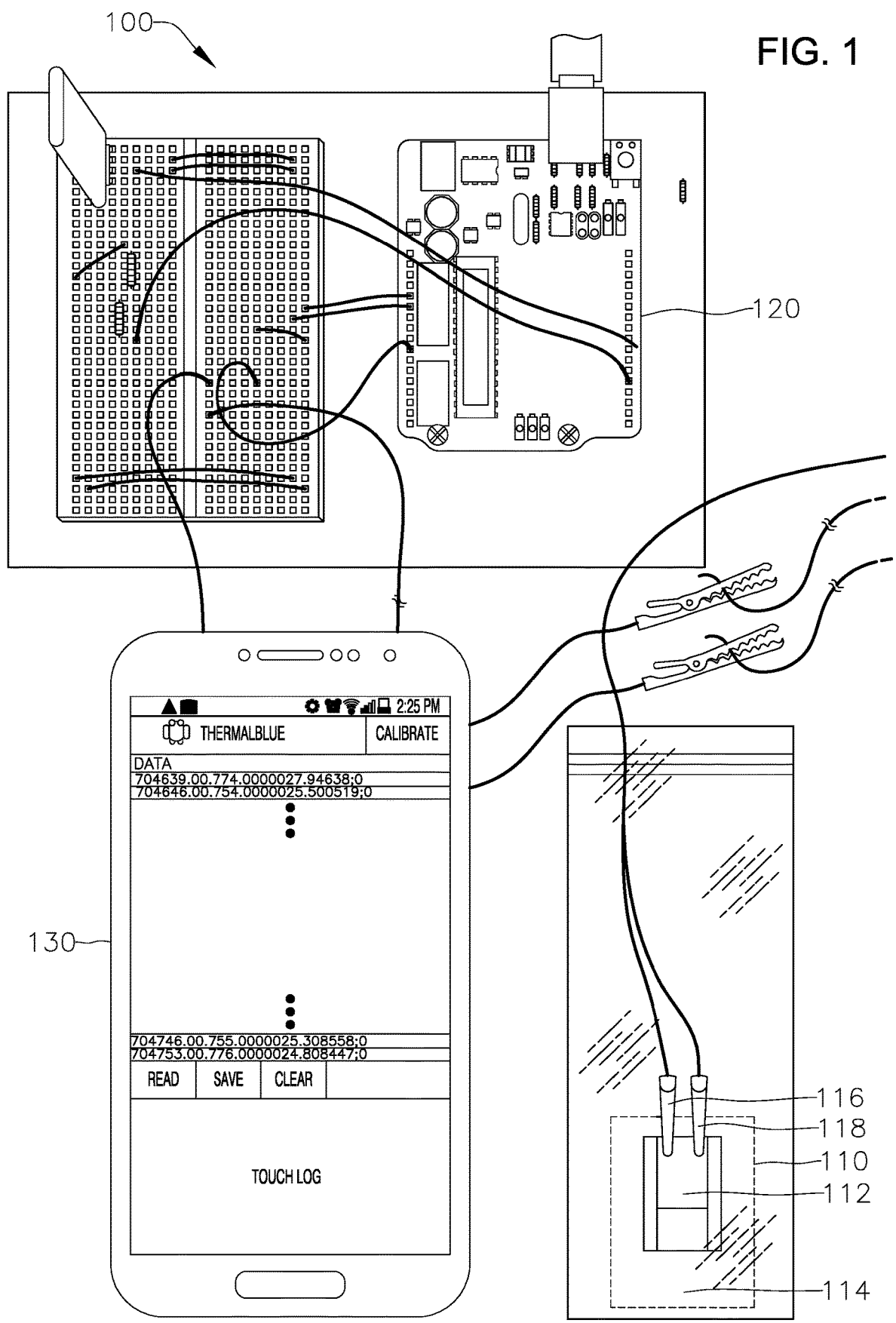
FIG. 1 is a photograph of a first exemplary sensing system including a first exemplary graphene oxide sensing element.

The exemplary embodiments described herein relate to sensors based on graphene oxide thin films, which sensors are operable to sense a condition (e.g., temperature, pressure) at a sensing location based on the electrical resistance of the sensors at the time of sensing. In an embodiment, a sensor including a graphene oxide sensing element may be used as a temperature sensor based on negative temperature coefficient ("NTC") behavior of graphene oxide. In an embodiment, a sensor including two graphene oxide sensing elements may be used as a pressure sensor based a relationship between applied pressure and contact area between such sensing elements. In an embodiment, a graphene oxide sensing element may be fabricated using a graphene oxide-containing ink. In an embodiment, an ink may be formulated by the dispersal of graphene oxide sheets in water. Such an ink may be used to print micropatterns on a flexible substrate using a commercial inkjet printer. In an embodiment, the flexible substrate may be made from a polyester. In an embodiment, the polyester may be polyethylene terephthalate ("PET"). In an embodiment, the flexible substrate may be a polyimide. In an embodiment, the polyimide may be poly(4,4'-oxydiphenylene-pyromellitimide), which is sold by E. I. du Pont de Nemours and Company of Wilmington, Del., under the trade name KAPTON. Graphene oxide micropatterns printed in this manner may be subsequently reduced to graphene either thermally or chemically. Thermal reduction may be conducted at 200-250° C. over a time interval ranging from minutes to hours using a heat source such as a heat lamp, oven or hot plate. Chemical reduction may be conducted with a reducing agent (e.g., hydrazine, etc.) using techniques that are known in the art. Various parameters of process may be tuned in order to control the resulting graphene oxide film's structure, and, therefore, its electrical resistance. These may include parameters of the printing process (e.g., the spacing between adjacent ink droplets, the number of printing layers, etc.) and/or parameters of the reduction process (e.g., the time and temperature of thermal reduction). In an embodiment, the resistance of a graphene oxide film may be reduced by spacing ink droplets more closely to one another and/or by increasing a number of printed layers. In an embodiment, the response time of a graphene oxide film (i.e., the time taken for the resistance of a graphene oxide film to stabilize at a given condition) may be reduced by decreasing a number of printed layers to produce a thinner graphene oxide film.

An exemplary graphene film produced as described above may behave as a NTC sensing element, exhibiting a decrease in electrical resistance corresponding to an increase in temperature. The NTC behavior of such a graphene film is described in commonly-owned U.S. Patent Application Publication No. 2014/0103298 to Lee et al., as well as in Kong et al., "Temperature-Dependent Electrical Properties of Graphene Inkjet-Printed on Flexible Materials," Langmuir, ACS Publications, American Chemical Society, 28 (2012), pp. 13467-13472, both of which are incorporated herein by reference in their entireties.

The exemplary embodiments additionally relate to the use of such graphene films for human physiological monitoring purposes. For example, small variations in skin temperature occur due to heat dissipation from blood flow; an exemplary NTC sensing element including a graphene oxide thin film exhibits sufficient sensitivity and sufficiently fast response time to sense temperature changes on the skin of a person originating from pulsatile blood flow. In an embodiment, an exemplary NTC sensing element can sense such temperature variations while wrapped around a subject's finger. In another embodiment, data collected from multiple sensors at different body locations (e.g., finger, chest and lower limbs) can be used to infer information similar to that measured by an electrocardiograph ("EKG"). In an embodiment, an exemplary NTC sensing element may be integrated into a wearable object such as a glove, a sock, a skullcap, or an undergarment. In an embodiment, an exemplary NTC sensing element is used for physiological monitoring in a medical application. In an embodiment, an exemplary NTC sensing element is used for physiological monitoring in a non-medical application such as a consumer monitoring device, a military monitoring device, and an athletic monitoring device.

FIG. 1 is a photograph of an exemplary system 100 including a patch-type flexible sensor 110. The flexible sensor 110 includes a graphene oxide thin film 112 deposited on a flexible substrate 114. In an embodiment, the flexible substrate 114 is made from a polyimide. In an embodiment, the flexible substrate 114 is made from polyethylene terephthalate. In an embodiment, the graphene oxide thin film 112 is deposited on the flexible substrate 114 through a technique including inkjet printing. In an embodiment, the graphene oxide thin film 112 is deposited on the flexible substrate 114 through a technique involving drop-casting. In an embodiment, the graphene oxide thin film 112 is thermally reduced. In an embodiment, the graphene oxide thin film 112 is chemically reduced. In another embodiment, the graphene oxide thin film 112 is deposited on the flexible substrate 114 through another suitable technique. The flexible sensor 110 also includes electrical connectors 116, 118 coupled to opposite sides of the graphene oxide thin film 112. In the embodiment shown in FIG. 1, the electrical connectors 116, 118 are adapted to be coupled to "alligator clip" type connectors, but those of skill in the art will understand that any other suitable type of electrical/mechanical connector may be used.

The flexible sensor 110 is coupled to a wireless transmitter 120 that is configured to transmit data to a smart phone 130 using a personal area network connection. In the embodiment shown in FIG. 1, the wireless transmitter 120 is an Arduino Uno transmitter manufactured by Arduino, LLC, of Somerville, Mass., and the personal area network operates under the IEEE 802.15.1 (i.e., Bluetooth) standard, but those of skill in the art will understand that these are only exemplary and that the exemplary flexible sensor 110 may be coupled to any other type of device suitable to receive and process the data measured thereby. In an embodiment, the wireless transmitter 120 is coupled to a voltage divider circuit that operates as an analog-to-digital converter measuring the change of voltage across the exemplary flexible sensor. In an embodiment, the smart phone 130 is configured to calculate the resistance of the flexible sensor 110, which may then be used to calculate the temperature of an object (e.g., a portion of a human body) to which the flexible sensor 110 is attached. For example, the smart phone 130 may be provided with software operative to calculate the resistance of the flexible sensor 110 based on the measured change of voltage, and to calculate the temperature based on the model for the NTC behavior of the flexible sensor 110 to be described below with reference to FIG. 5.

Figure 2:
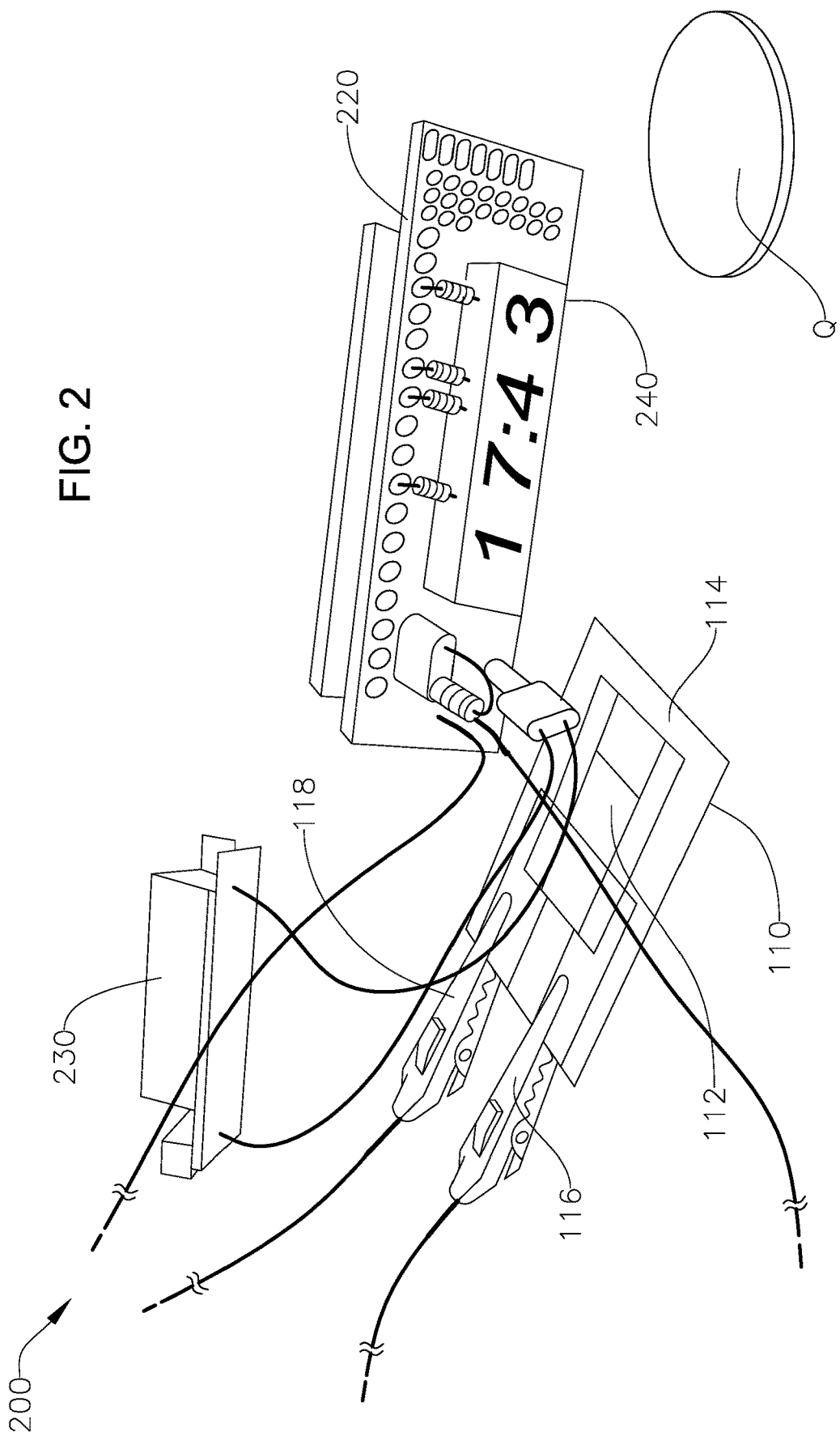
FIG. 2 is a photograph of a second exemplary sensing system including a second exemplary graphene oxide sensing element.

FIG. 2 is a photograph of an exemplary system 200 including a smaller circuit board that may be used to reduce the size of the exemplary system 200 as compared to that of the exemplary system 100 shown in FIG. 1. The system 200 includes the flexible sensor 110, as described above with reference to FIG. 1. In the system 200, the flexible sensor 110 is coupled to a microboard 220 (e.g., a small circuit board), which is coupled to a small standalone battery 230. The microboard 220 is configured to measure the electrical resistance of the flexible sensor 110, to compute a temperature (i.e., the temperature of an object to which the flexible sensor 110 is attached) based on the measured resistance, and to display the temperature on an LED screen 240. FIG. 2 also includes a quarter Q shown to indicate the size and scale of the system 200. In the system 200 shown in FIG. 2, the microboard 220 is an Arduino Micro microboard manufactured by Arduino, LLC, of Somerville, Mass., but those of skill in the art will understand that this is only exemplary. For example, the microboard 220 include hardware, software, firmware, or a combination thereof operative to calculate the resistance of the flexible sensor 110 based on the measured change of voltage, and to calculate the temperature based on the model for the NTC behavior of the flexible sensor 110 to be described below with reference to FIG. 5.

FIG. 3A is a schematic illustration of a further exemplary system 300. The exemplary system 300 includes a graphene oxide sensing element 310, a battery 320, a wireless transmission module 330, a plurality of contact readouts 340, and a display 350, all of which are disposed on a single flexible substrate 360. In another embodiment, the contact readouts 340 and/or the display 350 may be omitted to further reduce the size of the exemplary system 300. FIG. 3B is a perspective view of the exemplary system 300. It will be apparent to those of skill in the art that the elements of the exemplary system 300 may be coupled to one another by appropriate electrical connections.

FIG. 4 is a graph 400 illustrating the correlation between resistance and temperature for an exemplary NTC sensing element including a printed graphene sensor that may be fabricated according to the above-described technique. More particularly, the graph 400 includes a first plot 410 showing the relationship of resistance to temperature for printed graphene oxide and a second plot 420 showing the relationship of resistance to temperature for drop-casted graphene oxide. Both the first plot 410 and the second plot 420 show resistance in Ohms along a logarithmic scale 430 plotted against temperature in Kelvin along a scale 440. It may be observed from FIG. 4 that the resistance of the an exemplary printed graphene film decreases significantly with temperature.

Figure 5:
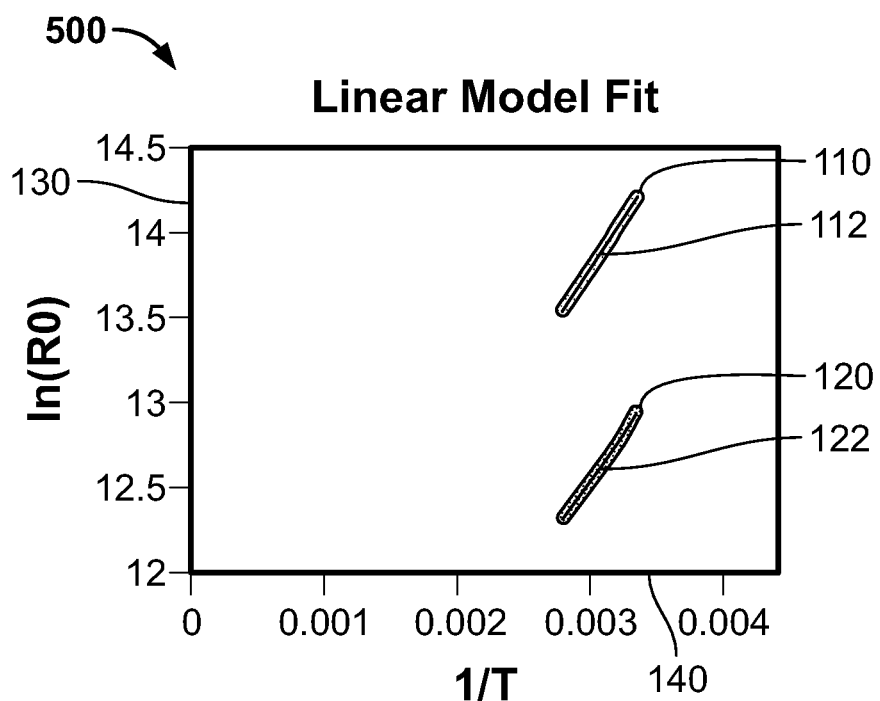
FIG. 5 is a graph showing analytical modeling of the temperature-dependence of an exemplary graphene oxide sensing element exhibiting NTC behavior.

FIG. 5 is a graph 500 showing a model fit of the NTC behavior observed for the exemplary printed graphene film and exemplary drop-casted graphene film. More particularly, the graph 500 includes a first plot 510 showing measured data representing the relationship of resistance to temperature for printed graphene oxide and a second plot 520 showing measured data representing the relationship of resistance to temperature for drop-casted graphene oxide. Both the first plot 510 and the second plot 520 show the natural logarithm of the resistance in Ohms along a scale 530 plotted against the inverse of the temperature in Kelvin along a scale 540. The equation $$R_T = R_0 \exp\left(B \frac{T_0 - T}{T \cdot T_0}\right)$$

may be used to model the NTC behavior represented by the plots 510, 520. In this equation, T is the temperature, $T_0$ is a reference temperature that is 298 K, $R_T$ is the electrical resistance as a function of the temperature T, B is a material constant that is a measure of temperature sensitivity, and $R_0$ is the resistance at the reference temperature $T_0$. Adapting this equation to multiple exemplary sensors of the present invention, it may be determined that B is in the range of 1100 K to 2500 K with respect to the range of electrical resistance from 10 kΩ to 20 MΩ.

Considering the model fit shown in the graph 500 of FIG. 5 in another manner, the model fit may be expressed as a linear relationship between the inverse of the temperature shown along the scale 540 and the natural logarithm of the resistance as shown along the scale 530. More particularly, for the plot 520 representing the NTC behavior of drop-casted graphene oxide, such NTC behavior may be modeled using the equation: y=1112.1x+9.1912. For the plot 510 representing the NTC behavior of printed graphene oxide, such NTC behavior may be modeled using the equation: y=1171.5x+10.255. In both of these equations, y is the natural logarithm of the resistance, in Ohms, of the graphene oxide sensing element being modeled, and x is the inverse of the temperature, in Kelvin, resulting in such resistance.

Figure 6:
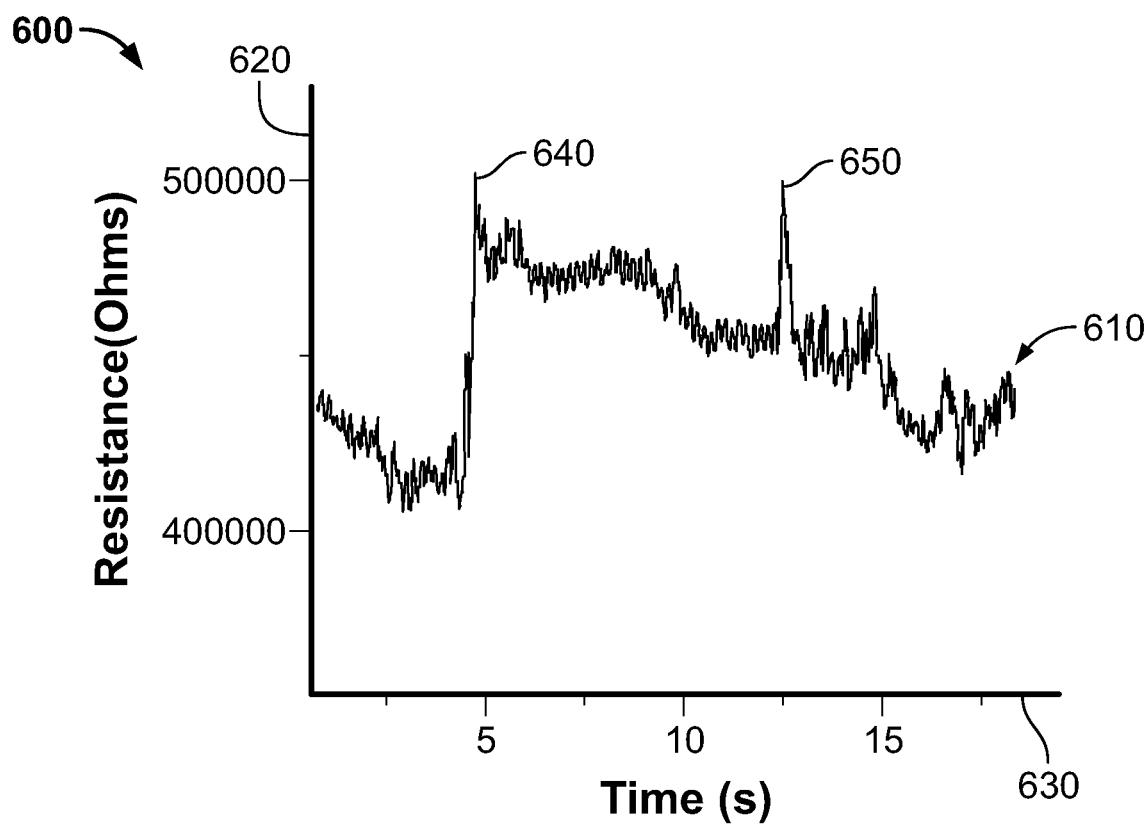
FIG. 6 is a graph showing resistance plotted against time when an exemplary graphene oxide sensing element exhibiting NTC behavior is pinched between a person's fingers.

FIG. 6 is a graph 600 showing resistance data collected with an exemplary sensor (e.g., the sensor 110 of FIG. 1) when the sensor is pinched between a person's index finger and thumb. More particularly, the graph 600 includes a plot 610 showing resistance in Ohms along a scale 620, plotted against time in seconds along a scale 630. The plot 610 includes a first point 640 at which the person's finger is pinched to reduce blood flow thereto and a second point 650 at which the sensor is released from between the person's finger. When blood flow is reduced and when the sensor is released from the person's finger, the electrical resistance increases due to the decrease of temperature, as may be expected due to the NTC characteristics of the sensor. It may be inferred that small decreases in temperature during this pinching experiment are caused by pulsatile blood flow in the person's fingers.

Figure 7:
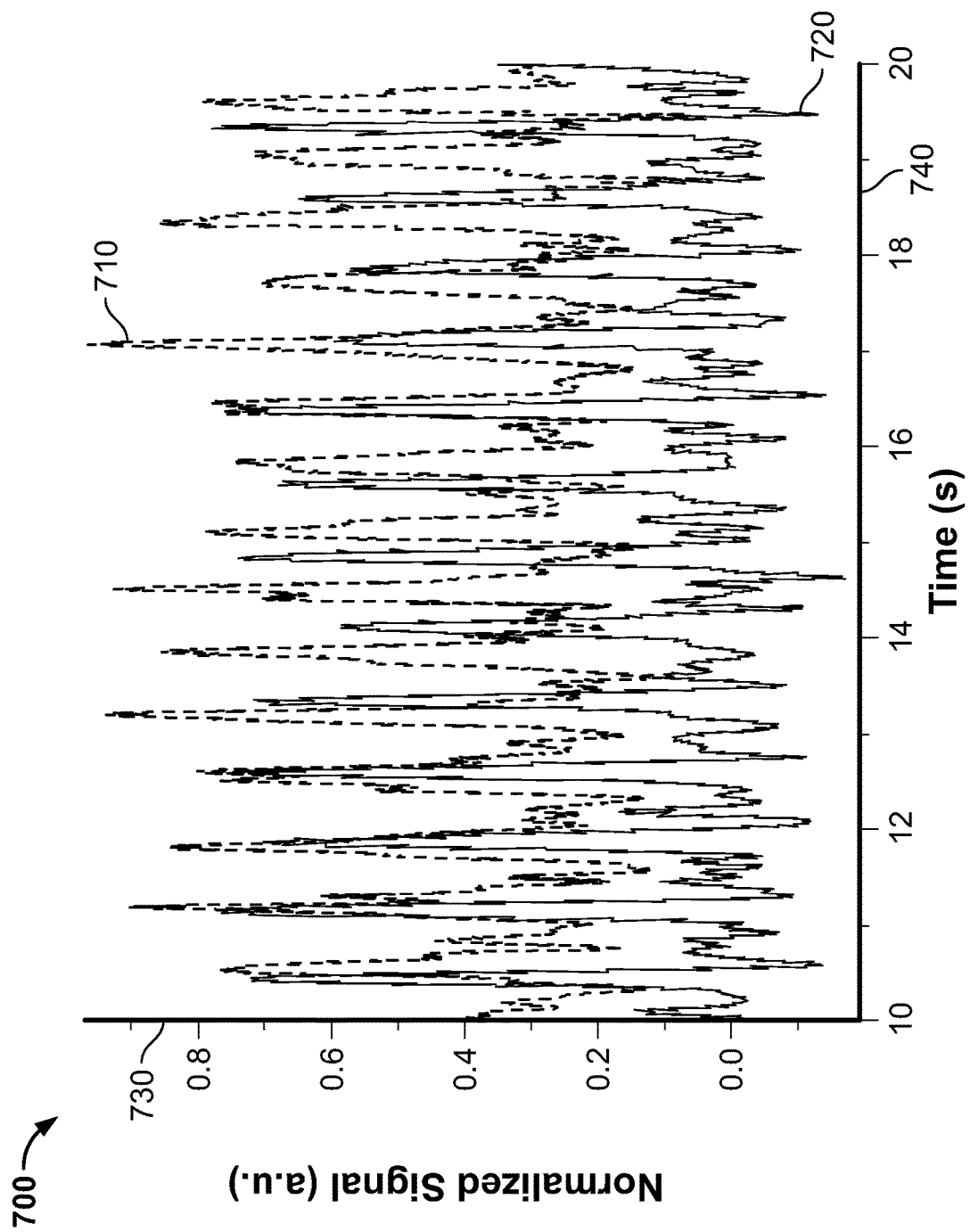
FIG. 7 is a graph comparing a normalized pulse signal measured by an exemplary graphene oxide sensing element exhibiting NTC behavior to that measured by a commercial pulse oximeter.

FIG. 7 shows a graph 700 comparing heartbeat measurements recorded with the exemplary system of FIG. 1 to those measured with a commercial pulse oximeter. In the experiment performed to generate FIG. 7, a subject's left index finger was attached to the exemplary sensor 110 of FIG. 1, while the right index finger was attached to a commercial heart rate sensor (e.g., a Pulse Sensor Amped sensor manufactured by Adafruit Industries of New York, N.Y.). The data collected by the exemplary sensor 110 and by the commercial heart rate sensor were filtered with a digital band pass and were normalized to compare the heart rate measured by the two sensors. The graph 700 includes a first plot 710 showing the heart rate measured by the exemplary sensor and a second plot 720 showing the heart rate measured by the commercial heart rate sensor. Both the first plot 710 and the second plot 720 are shown in normalized arbitrary units ("a.u.") along a scale 730, plotted against time in seconds along a scale 740. It may be observed that there is about a 6% mismatch between the plot 710 the plot 720. The mismatch between the heart rate as determined by the commercial heart rate sensor and that measured by the exemplary system of FIG. 1 was 6%, which remained constant for heart rates of about 80 beats per minute and about 130 beats per minute, and which is within the error of the commercial pulse oximeter.

Figure 8:
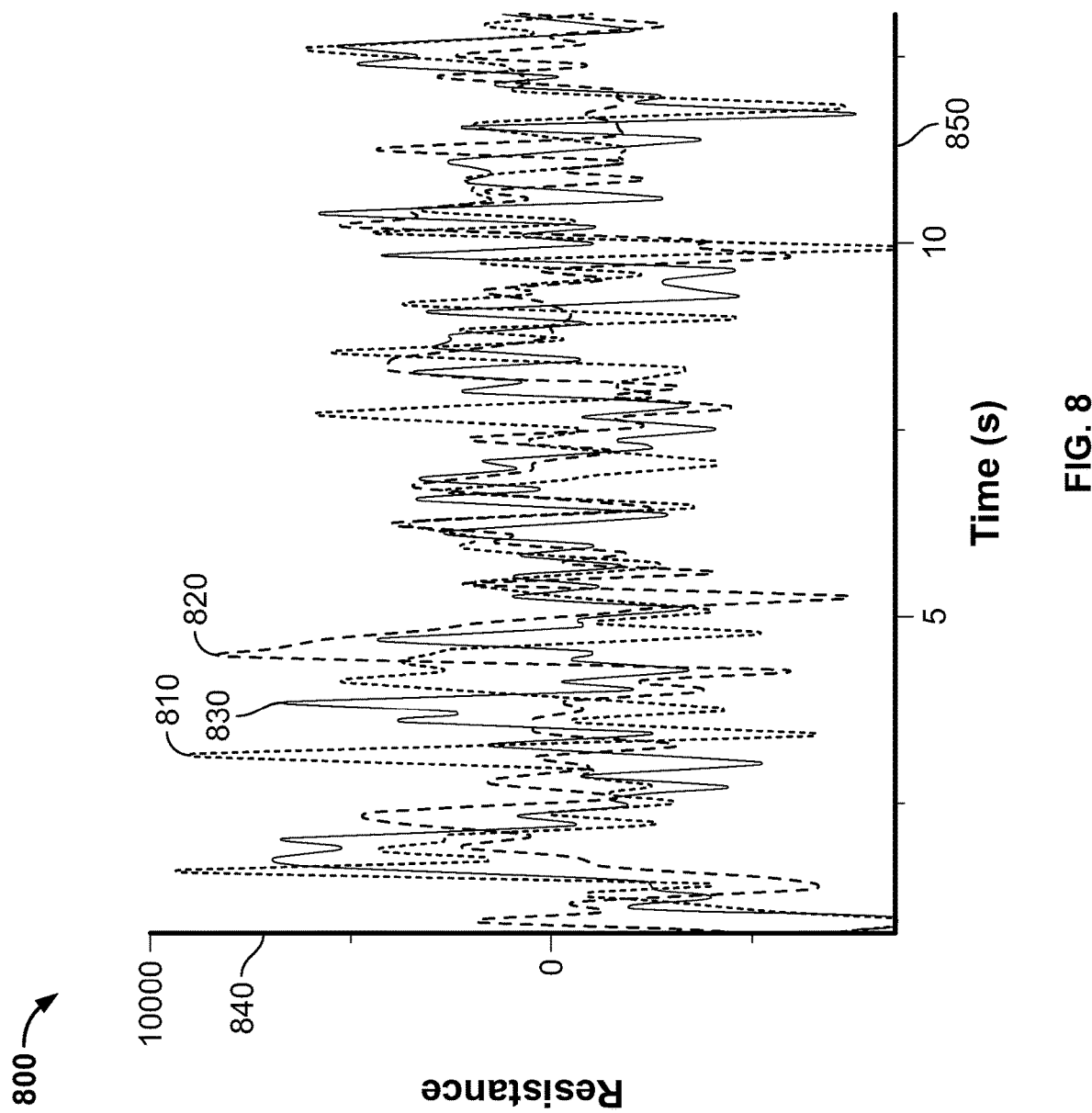
FIG. 8 is a graph showing pulse signals measured by an exemplary graphene oxide sensing element exhibiting NTC behavior at three locations on a patient's body.

FIG. 8 shows a graph 800 illustrating heartbeat measurements recorded with the exemplary system of FIG. 1 when the exemplary graphene-based sensor 110 is attached at different body locations. More particularly, FIG. 8 includes a first plot 810 showing data measured when the exemplary sensor 110 is attached to a subject's chest, a second plot 820 showing data measured when the exemplary sensor 110 is attached to a subject's fingertip, and a third plot 830 showing data measured when the exemplary sensor 110 is attached to a subject's wrist. Each of the plots 810, 820, 830 represents data that have been filtered using a 0.5-4 Hz bandpass filter; each is shown in measured resistance in Ohms along a scale 840, plotted against time in seconds along a scale 850. It may be observed that attachment of the exemplary sensor 110 at the patient's finger, data from which attachment is shown in plot 820, provides the most distinguishable data as a heart rate detector.

FIGS. 9A and 9B are photographs of an exemplary sensor 900 that is adapted for use as an electrode for electrocardiogram ("EKG") measurements. FIG. 9A shows the sensor 900 as viewed looking toward the side of the sensor 900 that contacts the patient's skin, while FIG. 9B shows the sensor 900 as viewed looking toward the side of the sensor 900 that faces away from the patient's skin. The sensor 900, like the exemplary sensors 110 and 120 described above, includes an inkjet-printed graphene oxide film 910 that has been deposited on a flexible substrate 920. In another embodiment, the graphene oxide film 920 may be deposited by a different technique, such as through the use of drop-casting rather than printing. In an embodiment, the graphene oxide film 910 may be thermally reduced. In an embodiment, the graphene oxide film 910 may be chemically reduced. In an embodiment, the flexible substrate 920 may be made from a polyimide. In an embodiment, the flexible substrate 920 may be made from polyethylene terephthalate. The sensor 900 also includes a snap electrode 930, which may be substantially similar to snap electrodes known in the art. The sensor 900 also includes insulating cloth medical tape 940 that is positioned so as to insulate the snap electrode 930 from a subject's skin when the sensor 900 is adhered thereto (e.g., through the application of medical tape), thereby ensuring that only the graphene oxide film 910 collects a signal.

Figure 10:
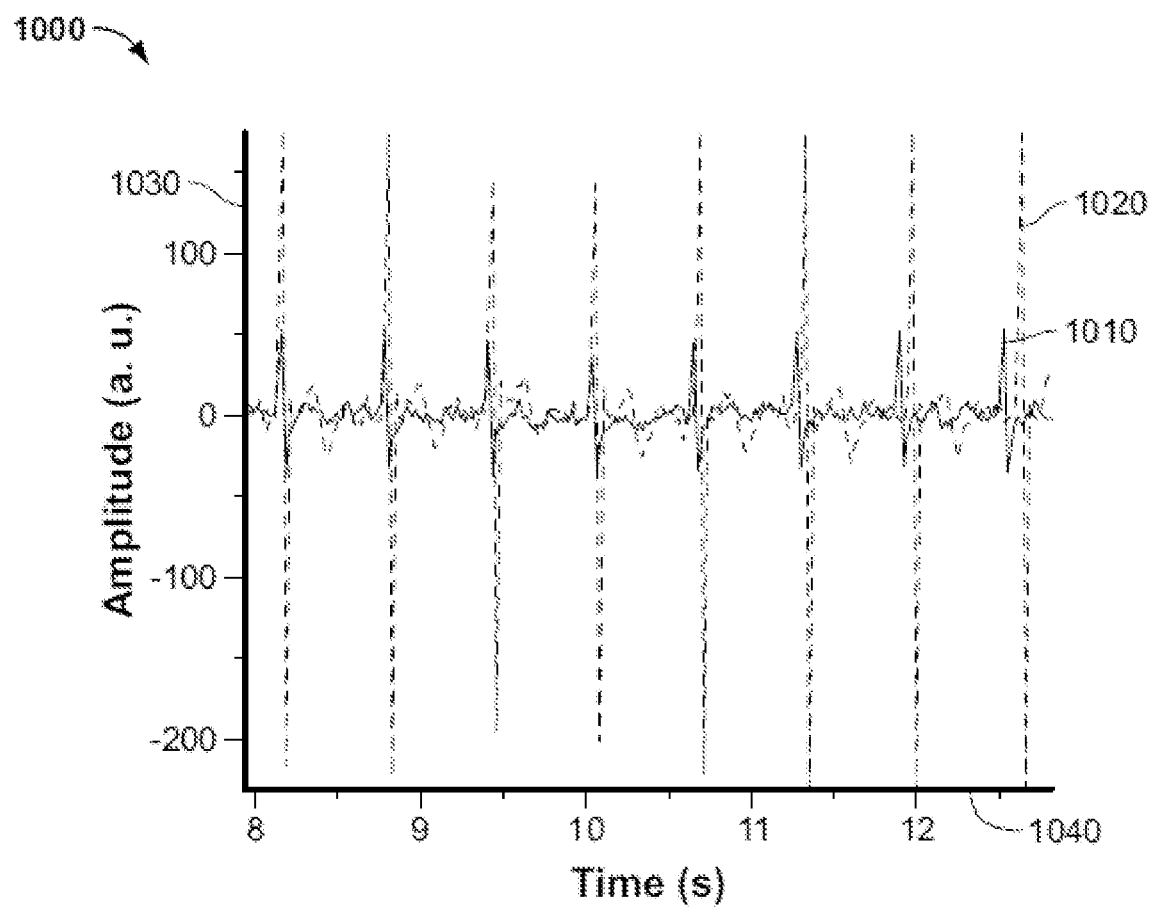
FIG. 10 is a graph comparing a electrocardiogram ("EKG") signal measured using a plurality of the fourth exemplary graphene oxide sensing elements as electrodes to that measured using Ag/AgCl electrodes.

FIG. 10 shows a plot 1000 comparing an EKG signal measured using sensors 900 as measurement electrodes to an EKG signal measured using electrodes consisting of an Ag/AgCl electrode surrounded by a conducting hydrogel adhesive. More particularly, the plot 1000 includes a first plot 1010 showing an EKG signal measured using exemplary sensors 900 and a second plot 1020 showing an EKG signal measured using Ag/AgCl electrodes. Both the first and second plots 1010, 1020 show data collected using a commercially available EKG device, and show signal amplitude 1030, in arbitrary units ("a.u."), plotted against time 1040, in seconds. From the plot 1000, it may be seen that the sensor 900 is suitable for use in EKG measurements. Moreover, the sensor 900 will not dry out or irritate a subject's skin, as will an Ag/AgCl electrode with a conducting hydrogel, rendering the sensor 900 more suitable for long-term monitoring.

Figure 11:
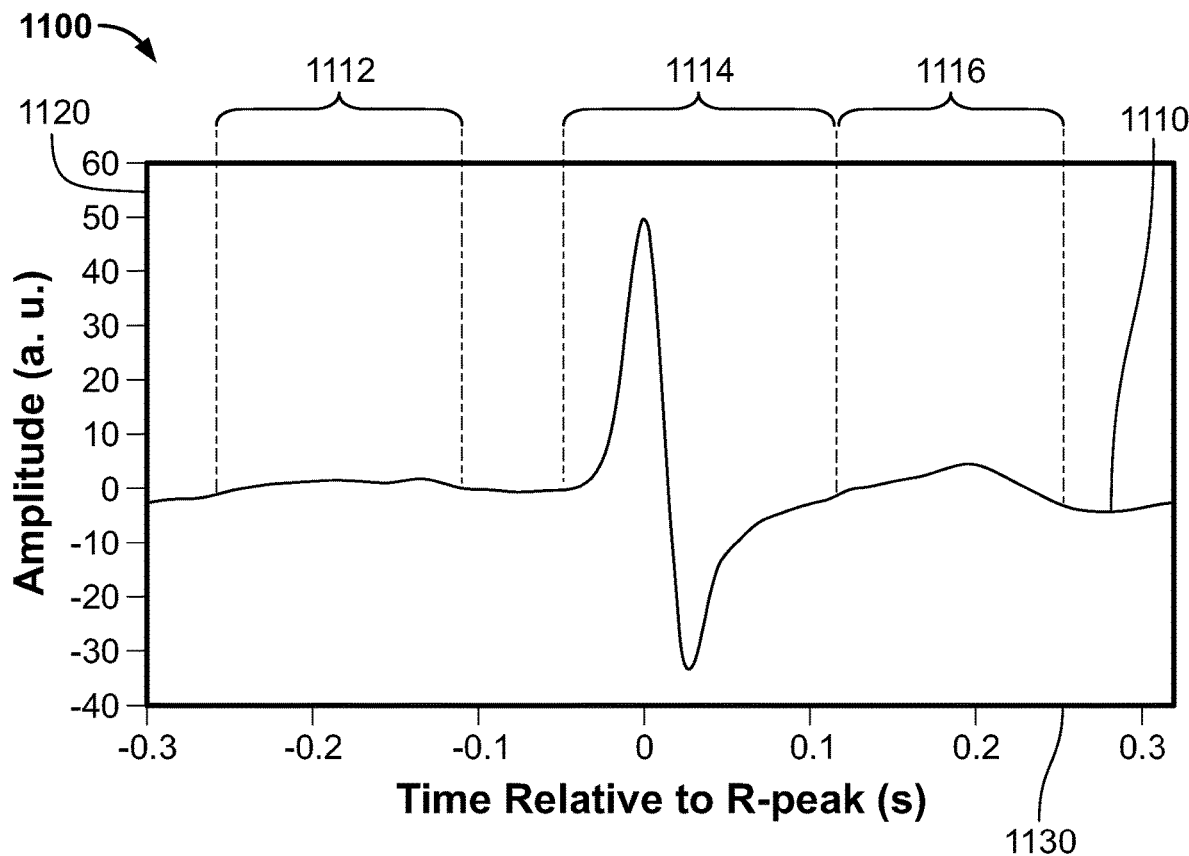
FIG. 11 is a graph showing a full cardiograph cycle of an EKG signal measured using a plurality of the fourth exemplary graphene oxide sensing elements as electrodes.

FIG. 11 shows a plot 1100 showing a full cardiac cycle 1110 as measured with the exemplary sensor 900. The plot 1100 shows signal amplitude 1120, as measured in arbitrary units ("a.u."), plotted against the time 1130, as measured in seconds relative to the R-peak of the cycle 1110. The cardiac cycle 1110 includes a P-wave 1112, a QRS complex 1114, and a T wave 1116, all of which are legible in the cardiac cycle 1110 measured using the exemplary sensor 900. It may therefore be seen that the sensor 900 measures electrical potential generated by the heart through direct electrical connection with the skin, and is therefore functional as an EKG electrode and provides the same information as traditional EKG electrodes.

In another embodiment, a sensor including graphene oxide may be adapted to sense pressure based on piezoresistive properties of graphene oxide. Such a sensor may include two separate graphene oxide elements, each of which is deposited on a corresponding substrate. Because of the porous structure of graphene oxide (e.g., chemically reduced graphene oxide), when such graphene oxide elements are pressed together, the contact surface therebetween increases, causing a corresponding reduction in electrical resistance.

Figure 12A:
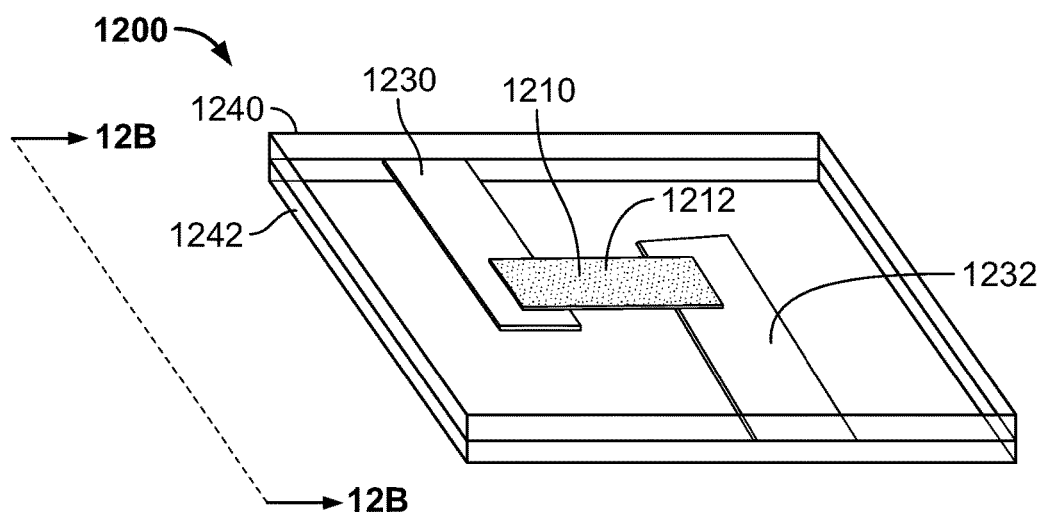
FIG. 12A is a perspective rendering of a fifth exemplary sensing system including a fifth exemplary graphene oxide sensing element.
Figure 12B:
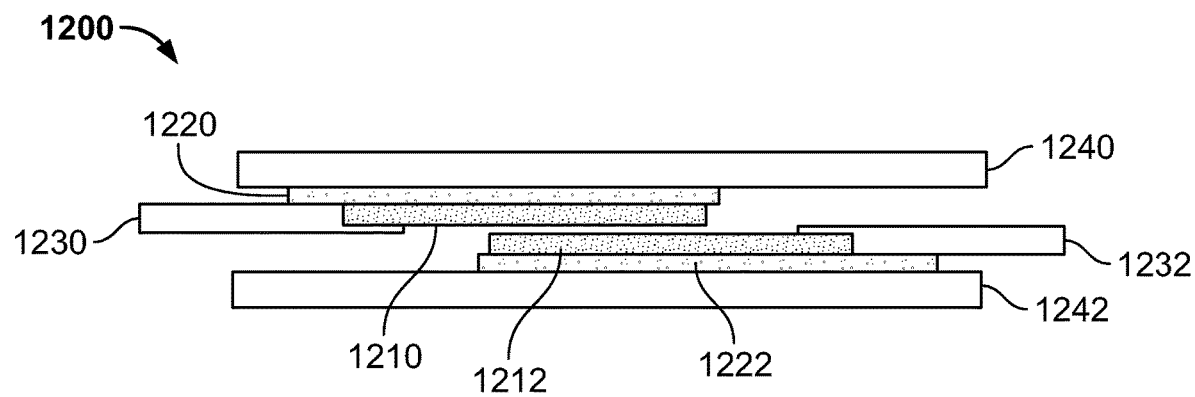
FIG. 12B is a cross-sectional view, taken along line 12B-12B, of the sensing system of FIG. 12A.

FIGS. 12A and 12B illustrate a perspective view and a cross-sectional view, respectively, of such a sensor 1200. The sensor 1200 includes first and second graphene oxide elements 1210 and 1212, which substantially overlap one another and are therefore shown as one in FIG. 12A. Each of the graphene oxide elements 1210, 1212 is deposited on a corresponding substrate 1220, 1222. In an embodiment, the substrates 1220, 1222 are made from a polyimide. In an embodiment, the substrates 1220, 1222 may be made from polyethylene terephthalate. In an embodiment, the substrates 1220, 1222 may be made from another suitable material. In an embodiment, the graphene oxide elements 1210, 1212 may be thermally reduced onto the corresponding ones of the substrates 1220, 1222. In an embodiment, the graphene oxide elements 1210, 1212 may be chemically reduced onto the corresponding ones of the substrates 1220, 1222. Each of the graphene oxide elements 1210, 1212 is coupled to a corresponding electrical connector 1230, 1232. In an embodiment, the electrical connectors 1230, 1232 are made from silver. In another embodiment, the electrical connectors 1230, 1232 are made from another suitable conducting material. The graphene oxide elements 1210, 1212 are positioned such that they overlay one another and are sandwiched between casing layers 1240, 1242. In an embodiment, the casing layers 1240, 1242 are made from a silicone material. In an embodiment, the silicone material is polydimethylsiloxane ("PDMS"). In an embodiment, the casing layers 1240, 1242 are made from a different material that is capable of conveying an applied pressure to the graphene oxide elements 1210, 1212 as described herein. In an embodiment, the casing layers 1240, 1242 are made from a flexible material.

Continuing to refer to FIGS. 12A and 12B, the sensor 1200 may be used by coupling the electrical connectors 1230, 1232 to a power source (e.g., a battery, a power supply, etc.) that applies a constant voltage. Current flowing through the graphene oxide elements 1210, 1212 (i.e., via the electrical connectors 1230, 1232) may be measured by any standard means. The resistance of the graphene oxide elements 1210, 1212 may be varied by applying a varying compressive force to the casing layers 1240, 1242, and the current resulting from the constant voltage being applied may vary accordingly. By measuring this current, the pressure being applied to the casing layers 1240, 1242 may therefore be inferred.

Figure 13:
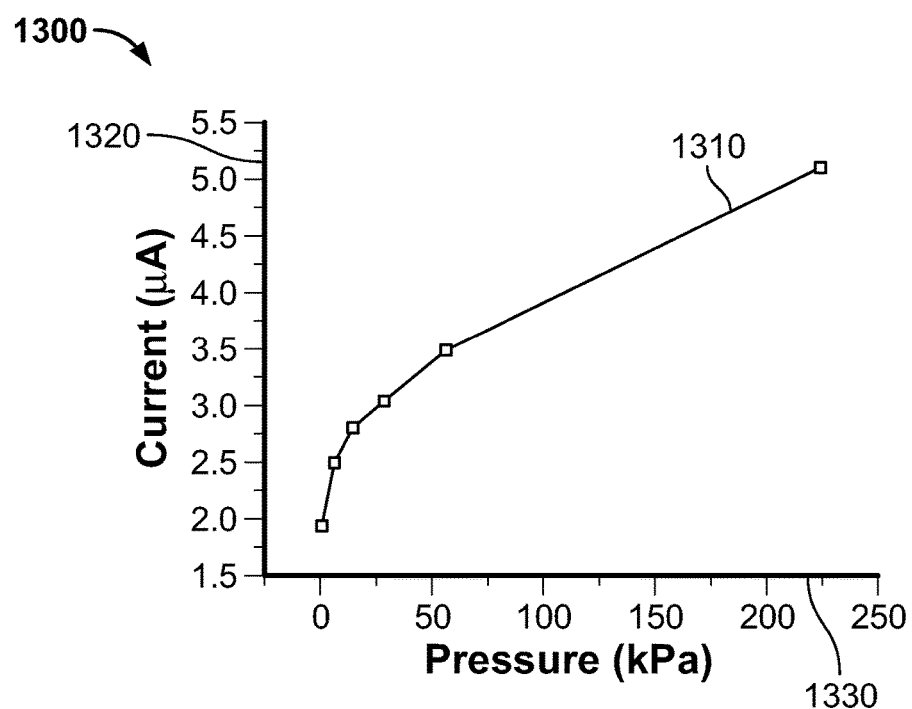
FIG. 13 is a graph showing current plotted against applied pressure for a constant voltage applied to the sensing system of FIG. 12A.

FIG. 13 is a graph 1300 including a plot 1310 showing the relationship of current to pressure for one embodiment of the sensor 1200, which included two sensors similar to the sensor 110, as described above with reference to FIG. 1, sandwiched together as described above with reference to FIGS. 12A and 12B. More particularly, the plot 1310 shows current through the graphene oxide elements 1210, 1212, in microamperes (μA), along a scale 1320, plotted against pressure applied to the casing layers 1240, 1242, in kilopascals (kPa), along a scale 1330. From FIG. 13 it may be seen that that, for one embodiment of the sensor 1200, the graphene oxide elements 1210, 1212 have a pressure sensitivity that is between 0.05 and 0.0003 $kPa^{-1}$ at low pressure. It may be apparent to those of skill in the art that the sensitivity of a sensor may be tuned by modifying porosity of the graphene oxide elements 1210, 1212, which may, in turn, be controlled by modifying the parameters of the deposition and reduction process as described above.

Figure 14:
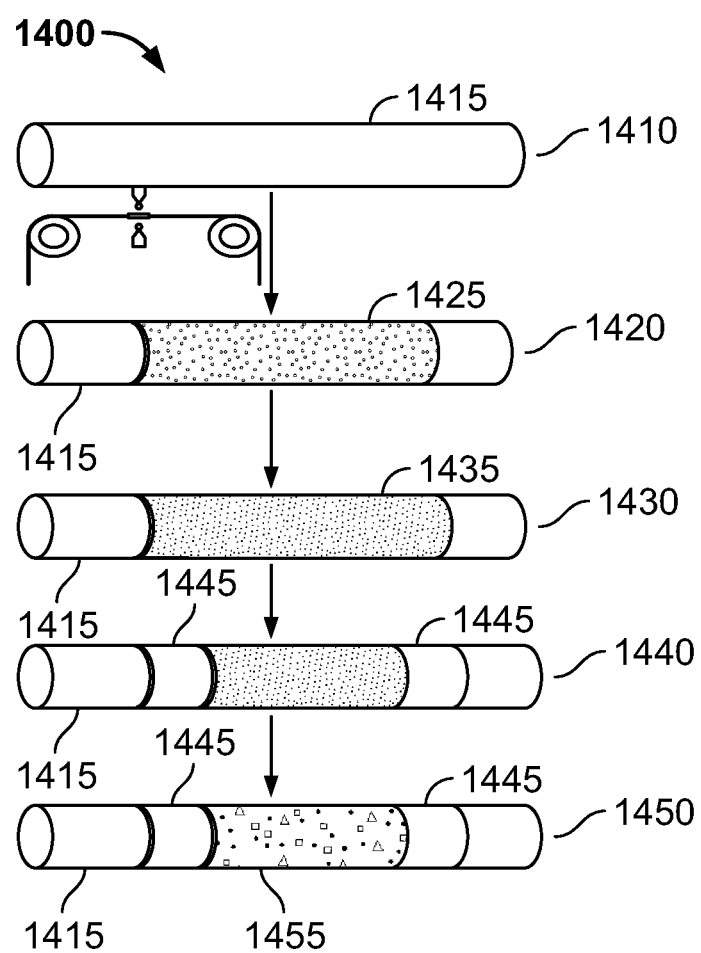
FIG. 14 is a schematic illustration of a process for fabricating a sixth exemplary graphene oxide sensing element.

In another embodiment, a sensor including graphene oxide may be provided on a flexible substrate having a fiber form factor, rather than one a flexible substrate having a patch form factor as described above with reference to FIGS. 1 and 2. FIG. 14 schematically illustrates stages in a process 1400 for coating a graphene oxide material onto a fiber to create a fiber-based sensor. In step 1410, a base fiber 1415 is provided. In an embodiment, the fiber 1415 is made from nylon. In another embodiment, the fiber 1415 is made from another suitable natural or synthetic fiber material (e.g., cotton, polyester, silk, wool, acrylic, acetate, etc.). In step 1420, a graphene oxide solution 1425 is printed onto the fiber 1415. In an embodiment, the graphene oxide solution 1425 is inkjet printed onto the fiber 1415 as described above. In step 1430, the graphene oxide solution 1425 is reduced to produce a graphene oxide coating 1435. In an embodiment, the graphene oxide solution 1425 is chemically reduced. In an embodiment, the graphene oxide solution 1425 is chemically reduced in an ascorbic acid solution. In step 1440, electrical connectors 1445 are coated onto the graphene oxide coating 1435. In an embodiment, the electrical connectors 1445 are manually coated onto the graphene oxide coating 1435 by the manual application of a conductive epoxy. In an embodiment, the electrical connectors 1445 are coated onto the graphene oxide coating 1435 by inkjet printing of silver nanoparticles. In an embodiment, the electrical connectors 1445 are made from silver. In an embodiment, the electrical connectors 1445 are made from another suitable conductor. In step 1450, a casing layer 1455 is coated onto the graphene oxide coating 1435. In an embodiment, the casing layer 1455 is made from a silicone material. In an embodiment, the silicone material is PDMS. In an embodiment, the casing layer 1455 is made from a poly(p-xylylene) polymer. In an embodiment, the poly(p-xylylene) polymer is the poly(p-xylylene) polymer sold by Specialty Coating Systems, Inc. of Indianapolis, Ind., under the trade name PARYLENE-D. In an embodiment, the casing layer 1455 is applied to the graphene oxide coating 1435 by coating a liquid coating onto the graphene oxide coating 1435, and placing the fiber 1415 into an oven (e.g., an oven at 70° C.) to cure.

Figure 15:
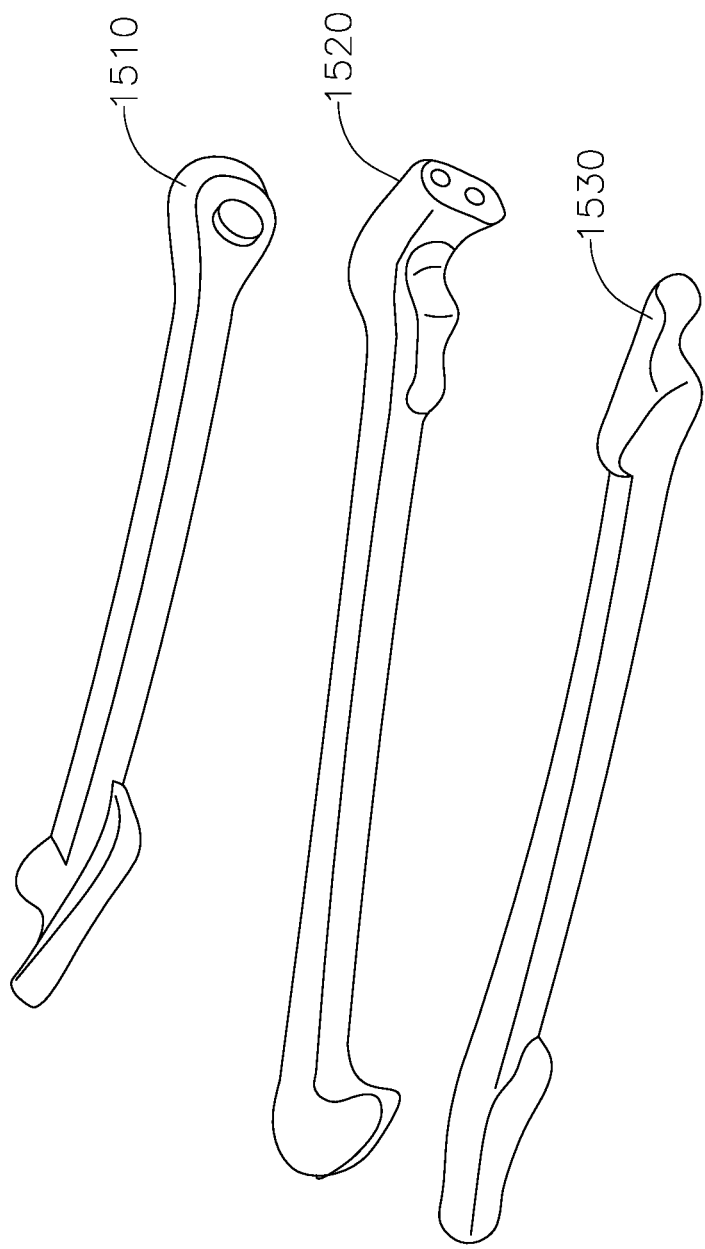
FIG. 15 is a photograph of sensing elements fabricated using the process of FIG. 14.

The method schematically shown in FIG. 14 may produce a graphene oxide-based sensor that is sensitive to temperature in the same manner as described above with reference to the sensor 110. In an embodiment, the method schematically shown in FIG. 14 may produce a graphene oxide-based sensor that is sensitive to pressure through the use of two graphene oxide elements pressed against one another as described with reference to FIGS. 12A and 12B. FIG. 15 is a photograph of three exemplary sensors 1510, 1520, 1530 that have been fabricated as described above with reference to FIG. 14.

The exemplary embodiments describe graphene-oxide based sensors and the fabrication and use thereof. Such sensors exhibit NTC behavior with high temperature sensitivity and fast response time, and may be useful for physiological monitoring applications. In another embodiment, such sensors are operative to sense pressure applied thereto. In one embodiment, an exemplary sensor may measure a subject's heart rate with error comparable to or better than a commercially available heart rate sensor. In another embodiment, an exemplary sensor may be used as an EKG electrode. Because of the molecular layer thickness of reduced graphene oxide, sensors fabricated therewith may be thin, flexible, and transparent, rendering them suitable for use in wearable sensor applications.

It should be understood that the embodiments described herein are merely exemplary in nature and that a person skilled in the art may make many variations and modifications thereto without departing from the scope of the present invention. All such variations and modifications, including those discussed above, are intended to be included within the scope of the invention.

We claim:

1. A sensing system, comprising:
   a sensor, including a single fiber flexible substrate having a longitudinal axis, a first end arranged along said longitudinal axis and a second end arranged along said longitudinal axis, said second end being spaced from said first end, a graphene oxide sensing element deposited directly on and in contact with at least a partial length of said single fiber flexible substrate between said first end thereof and said second end thereof, a first electrical connector formed from an electrically conductive material other than graphene oxide deposited on said first end of said single fiber flexible substrate, said first electrical connector being a coating for a first end of said graphene oxide sensing element, and a second electrical connector formed from the electrically conductive material other than graphene oxide deposited on said second end of said single fiber flexible substrate, said second electrical connector being a coating for a second end of said graphene oxide sensing element;

a power source coupled to said first and second electrical connectors of said sensor, said power source adapted to apply a constant voltage to said sensor;

a measurement element, communicatively coupled to said sensor and configured and arranged to measure an electrical current in said graphene oxide sensing element due to said constant voltage; and a calculation element, communicatively coupled to said measurement element and including a non-transitory computer-readable storage medium storing a set of instructions and a processor operative to execute said set of instructions, said set of instructions, when executed by said processor, causing said processor to calculate an electrical resistance of said graphene oxide sensing element based on said electrical current and said constant voltage and to calculate a condition for said graphene oxide sensing element at a location of said sensor based on a relationship between said electrical resistance and said condition.

2. The sensing system of claim 1, wherein said condition is temperature.

3. The sensing system of claim 2, wherein said processor determines a temperature using a linear relationship between a natural logarithm of said electrical resistance of said graphene oxide sensing element and an inverse of said temperature.

4. The sensing system of claim 2, wherein said single fiber flexible substrate is adapted to be affixed to a person's skin.

5. The sensing system of claim 2, wherein said processor calculates a plurality of temperatures, each of said plurality of temperatures being calculated at a corresponding one of a plurality of times.

6. The sensing system of claim 2, wherein said processor is configured to determine a pulse rate for a person based on changes in said electrical resistance, said changes in said electrical resistance due to temperature changes of said sensor associated with pulsatile blood flow in a person who is coupled to said sensor, said pulsatile blood flow being associated with said pulse rate.

7. The sensing system of claim 2, wherein said sensor is configurable as an EKG electrode by positioning said sensor to measure electrical potential generated by a heart through direct electrical connection with a patient's skin.

8. The sensing system of claim 1, wherein said condition is pressure.

9. A sensor, comprising:
a single fiber flexible substrate having a longitudinal axis, a first end arranged along said longitudinal axis and a second end arranged along said longitudinal axis, said second end being spaced from said first end;

a graphene oxide sensing element deposited directly on and in contact with at least a partial length of said single fiber flexible substrate between said first end thereof and said second end thereof;

a first electrical connector formed from an electrically conductive material other than graphene oxide deposited on said single fiber flexible substrate proximate said first end thereof, said first electrical connector being a coating for a first end of said graphene oxide sensing element; and a second electrical connector formed from the electrically conductive material other than graphene oxide deposited on said single fiber flexible substrate proximate said second end thereof, said second electrical connector being a coating for a second end of said graphene oxide sensing element, wherein said graphene oxide sensing element has an intermediate segment between said first end thereof and said second end thereof.

10. The sensor of claim 9, wherein said single fiber flexible substrate is made from one of a polyester and a polyimide.

11. The sensor of claim 9, wherein said single fiber flexible substrate is a cotton fiber, polyester fiber, silk fiber, wool fiber, acrylic fiber, or acetate fiber.

12. The sensor of claim 9, wherein said graphene oxide sensing element is deposited on said single fiber flexible substrate by inkjet printing a graphene oxide solution on said single fiber flexible substrate.

13. The sensor of claim 12, wherein after printing the graphene oxide solution, the printed graphene oxide solution is reduced to produce a graphene oxide coating, and wherein the first electrical connector and the second electrical connector are each inkjet printed onto the graphene oxide coating.

14. The sensor of claim 9, wherein the electrically conductive material other than graphene oxide is a conductive epoxy applied to the graphene oxide sensing element.

15. The sensor of claim 9, further comprising a casing layer provided on said intermediate segment of said graphene oxide sensing element.

16. The sensor of claim 9, wherein said single fiber flexible substrate further comprises a first cross section at said first end of said graphene oxide sensing element and a second cross section at said second end said graphene oxide sensing element, and
wherein said first electrical connector fully encloses said first end of the graphene oxide sensing element such that said first electrical connector circumscribes the first cross section, and
wherein said second electrical connector fully encloses said second end of the graphene oxide sensing element such that said second electrical connector circumscribes the second cross section.

* * * * *